United States Patent
Tamano et al.

(10) Patent No.: US 7,691,065 B2
(45) Date of Patent: Apr. 6, 2010

(54) ULTRASONIC PROBE AND ULTRASONIC DIAGNOSTIC DEVICE

(75) Inventors: Satoshi Tamano, Chiba (JP); Akibiko Hanaoka, Ibaraki (JP); Hideki Okazaki, Chiba (JP); Takashi Kobayashi, Chiba (JP); Sachie Yoshida, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/563,086

(22) PCT Filed: Jul. 2, 2004

(86) PCT No.: PCT/JP2004/009434

§ 371 (c)(1),
(2), (4) Date: Dec. 30, 2005

(87) PCT Pub. No.: WO2005/002449

PCT Pub. Date: Jan. 13, 2005

(65) Prior Publication Data

US 2006/0173310 A1    Aug. 3, 2006

(30) Foreign Application Priority Data

Jul. 3, 2003    (JP) .............................. 2003-191095

(51) Int. Cl.
*A61B 8/00*    (2006.01)
(52) U.S. Cl. ...................... 600/459; 600/447; 600/462
(58) Field of Classification Search ................. 600/459, 600/462, 444; 73/641; 367/7
See application file for complete search history.

(56) References Cited

U.S. PATENT DOCUMENTS 4,293,934 A * 10/1981 Herolz et al. ................. 367/27
4,917,097 A *  4/1990 Proudian et al. ............ 600/463

(Continued)

FOREIGN PATENT DOCUMENTS

JP    61-135639    6/1986

(Continued)

OTHER PUBLICATIONS

Edited by The Japan Society of Ultrasonics in Medicine, "Shin Choonpa Igaku 1 Iyo. Choonpa no Kiso", first edition, Igaku-Shoin Ltd., May 15, 2000, pp. 37 to 42.

*Primary Examiner*—Eric F Winakur
*Assistant Examiner*—Helene Bor
(74) *Attorney, Agent, or Firm*—Cooper & Dunham LLP (57) ABSTRACT

In an ultrasonic probe including an insert section which is to be inserted into a body cavity organ of a subject and a handle section which is coupled with the insert section, a plurality of vibrator elements (104) are disposed at a tip end of the insert section over the entire 360 degree circumference thereof and in the handle section, a connection change over switch (105) is disposed which successively changes over the electrical connection of a predetermined number of the vibrator elements among the plurality of the vibrator elements to be connected with a predetermined number of ultrasonic wave transmission and reception channels (701,702) in an ultrasonic diagnostic apparatus main body for transmitting and receiving ultrasonic wave signals. Accordingly, an ultrasonic probe which permits to collect ultrasonic wave images including tomograms and blood flow images of high quality without positional irregularity over the entire circumference of the insert section of the ultrasonic probe and to display the same, and an ultrasonic diagnostic apparatus using the same are obtained.

9 Claims, 6 Drawing Sheets

U.S. PATENT DOCUMENTS

| | | | |
|---|---|---|---|
| 5,027,659 A * | 7/1991 | Bele et al. | 73/626 |
| 5,060,651 A * | 10/1991 | Kondo et al. | 600/443 |
| 5,081,993 A * | 1/1992 | Kitney et al. | 600/455 |
| 5,099,850 A * | 3/1992 | Matsui et al. | 600/463 |
| 5,164,548 A * | 11/1992 | Angehrn | 181/103 |
| 5,291,892 A * | 3/1994 | O'Donnell | 600/454 |
| 5,349,960 A * | 9/1994 | Gondo | 600/455 |
| 5,456,259 A * | 10/1995 | Barlow et al. | 600/459 |
| 5,509,417 A * | 4/1996 | Dias et al. | 600/459 |
| 5,630,416 A * | 5/1997 | Uchikura et al. | 600/444 |
| 5,685,311 A * | 11/1997 | Hara | 600/459 |
| 5,787,049 A * | 7/1998 | Bates | 367/7 |
| 5,876,345 A * | 3/1999 | Eaton et al. | 600/466 |
| 6,045,508 A * | 4/2000 | Hossack et al. | 600/447 |
| 6,059,731 A * | 5/2000 | Seward et al. | 600/459 |
| 6,171,248 B1 * | 1/2001 | Hossack et al. | 600/459 |
| 6,511,431 B2 * | 1/2003 | Ohara et al. | 600/453 |
| 6,755,791 B2 * | 6/2004 | Kawashima | 600/467 |

FOREIGN PATENT DOCUMENTS

| | | |
|---|---|---|
| JP | 8-56948 | 3/1996 |
| JP | 11-56835 | 3/1999 |
| JP | 2003-180697 | 7/2003 |

* cited by examiner

Ultrasonic Wave Transmission/Reception Direction : 0 transducer129 disconnected
disconnected
disconnected
transducer160 disconnected
transducer161 disconnected
disconnected
disconnected
transducer192 disconnected
transducer193 disconnected
disconnected
disconnected
transducer224 disconnected
transducer225
transducer256
transducer1
transducer32
transducer33 disconnected
disconnected
disconnected
transducer64 disconnected
transducer65 disconnected
disconnected
disconnected
transducer96 disconnected
transducer97 disconnected
disconnected
disconnected
transducer128 disconnected Ultrasonic Wave Transmission/Reception Signals Ultrasonic Wave Reception ch32
Ultrasonic Wave Reception ch1
Ultrasonic Wave Delay Amount

Fig. 3(b)

Ultrasonic Wave Transmission/Reception Direction : 1 transducer129 disconnected
disconnected
disconnected
transducer160 disconnected
transducer161 disconnected
disconnected
disconnected
transducer192 disconnected
transducer193 disconnected
disconnected
disconnected
transducer224 disconnected
transducer225
transducer226
transducer256
transducer1
transducer32
transducer33 disconnected
disconnected
disconnected
transducer64 disconnected
transducer65 disconnected
disconnected
disconnected
transducer96 disconnected
transducer97 disconnected
disconnected
disconnected
transducer128 disconnected Ultrasonic Wave Transmission/Reception Signals Ultrasonic Wave Reception ch32
Ultrasonic Wave Reception ch1
Ultrasonic Wave Delay Amount

ULTRASONIC PROBE AND ULTRASONIC DIAGNOSTIC DEVICE

FIELD OF THE INVENTION

The present invention relates to an ultrasonic probe and an ultrasonic diagnostic apparatus and, in particular, relates to an improvement in an ultrasonic probe that is suitable for inserting into a body cavity (hereinafter "body cavity use ultrasonic probe") and for collecting ultrasonic images of the entire circumference of 360 degrees in the body cavity and an improvement in an ultrasonic diagnostic apparatus using the same.

CONVENTIONAL ART

A conventional body cavity use ultrasonic probe, as, for example, disclosed in JP-A-8-56948, is constituted in such a manner that through mechanically rotating an insert section of an ultrasonic probe around a longitudinal axis thereof ultrasonic images around the entire circumference of the insert section are collected.

Namely, the body cavity use ultrasonic probe as described in JP-A-8-56948 is constituted in such a manner that the insert section is formed in a hollow substantial cylindrical structure, and a flexible shaft is passed through the hollow portion from the tip portion to the handle portion thereof, ultrasonic transducers are disposed at the tip portion of the flexible shaft as well as a motor which is disposed at the handle portion of the ultrasonic probe is connected to the other end side thereof.

Accordingly, the body cavity use ultrasonic probe as described in JP-A-8-56948 is constituted in such a manner that through rotation of the motor the flexible shaft is rotated with reference to the center axis thereof, thereby, the ultrasonic transducers disposed at the tip portion are rotated. As a result, the irradiation direction of ultrasonic wave beams transmitted and received by the ultrasonic transducers is constituted so as to rotate and scan around the center of the insert section.

Further, JP-A-61-135639 discloses a device and method with which blood flow information within a blood vessel obtained by means of ultrasonic wave pulse Doppler method is displayed in two dimensions.

The insert section of the conventional ultrasonic probe used for a body cavity is formed by a flexible member so as to reduce a load to a subject and through deformation of the flexible shaft in accordance with deformation of the insert section, an insertion of the ultrasonic probe which is adaptable to the shape of a body cavity to be inserted was enabled.

As has been explained above, the ultrasonic probe as described in JP-A-8-56948 is constituted in such a manner that the motor rotation causes to rotate the ultrasonic transducers via the flexible shaft. For this reason, when the insert section is bent, since an irregularity in transfer torque by the flexible shaft is caused, there arose a problem that an irregularity in rotation of the ultrasonic transducers is likely caused. Namely, since the ultrasonic probe is constituted in such a manner that the stability of the scanning speed in the scanning direction of ultrasonic wave beam transmission and reception is determined by the stability of the rotation of the ultrasonic transducers via the flexible shaft, an irregularity in the ultrasonic wave beam transmission and reception is resulted in, for this reason, there arose even a tomographic image which is not required a comparatively high positional accuracy gives a 360 degree display image in which a "positional irregularity" is caused. Particularly, in order to obtain Doppler blood flow images that require the positional accuracy of the vibrators, it is necessary to transmit and receive signals while mechanically fixing the ultrasonic wave signal transmission and reception position of the vibrators correctly (or precisely) (so as not to vary the position during the ultrasonic wave signal transmission and reception). Further, it is necessary to transmit and receive ultrasonic wave signals while changing correctly and momentary (in about 15 micro seconds) the positions of the vibrators at every timing of the ultrasonic wave signal transmission and reception. For this reason, with the conventional scheme in which the ultrasonic transducers are mechanically rotated by making use of the flexible shaft, a blood flow image displaying was difficult.

An object of the present invention is to provide an ultrasonic probe that is capable of displaying ultrasonic wave images with no positional irregularity and with a high image quality including tomographic images and blood flow images along the entire circumference of the ultrasonic transducers, and an ultrasonic diagnostic apparatus using the same.

Another object of the present invention is to provide an ultrasonic diagnostic apparatus which permits to easily grasp the situation of disease, to reduce time required for diagnosis and to enhance diagnostic efficiency as well as permits to reduce a load for a subject, permits to easily confirm a disease situation with an ample blood flow such as malignant tumor and permits to obtain useful information for confirmed diagnosis.

SUMMARY OF THE INVENTION

In the present invention, m pieces of vibrator elements are disposed around the entire circumference of 360 degree at a tip of an insert section of an ultrasonic probe, ultrasonic wave signals from n (n<m) pieces of ultrasonic wave transmission and reception channels in an ultrasonic diagnostic apparatus main body are transmitted and received via connection change over switches by an array of a (where a is a number of nieces of continuing vibrator elements and a≈m/8–m/2) pieces of continuing vibrator elements among the in pieces of vibrator elements; and thereby, through successively changing transmission and reception directions of the ultrasonic wave signals by successively changing over the connection change over switches, ultrasonic wave images including ultrasonic wave tomographic images and ultrasonic blood flow images along the entire 360 degree circumference of the insert section of the ultrasonic probe can be obtained.

According to the present invention, since the change over of the ultrasonic wave transmission and reception direction is performed by selecting any of vibrator elements feeding the ultrasonic wave signals with the connection change over switches, the conventional image quality reduction due to the mechanical rotational movement of the ultrasonic wave transmission and reception direction can be prevented as well as since ultrasonic wave transmission and reception in a predetermined direction can be easily set, an acquisition of blood flow information such as color flow mapping (CFM) can be easily realized. Through displaying blood flow images along the 360 degree entire circumference of the ultrasonic probe based on the acquired blood flow information, ultrasonic wave images can be observed in real time, thereby, an examiner can easily grasp the situation of disease, time required for diagnosis is reduced and diagnostic efficiency can be enhanced as well as a load on a subject can be reduced.

Further, according to the present invention, since the number of ultrasonic wave signal transmission and reception channels each of which constitutes an ultrasonic wave signal transmission and reception unit for controlling feeding of transmission and reception wave signals to the ultrasonic

BEST MODES FOR CARRYING OUT THE INVENTION

Embodiments of the present invention will be explained with reference to drawings.

Further, in all of the drawings for explaining the embodiments of the present invention, ones having the same functions are assigned the same reference numerals and the repetitive explanation thereof is omitted.

Embodiment 1

Figure 1:
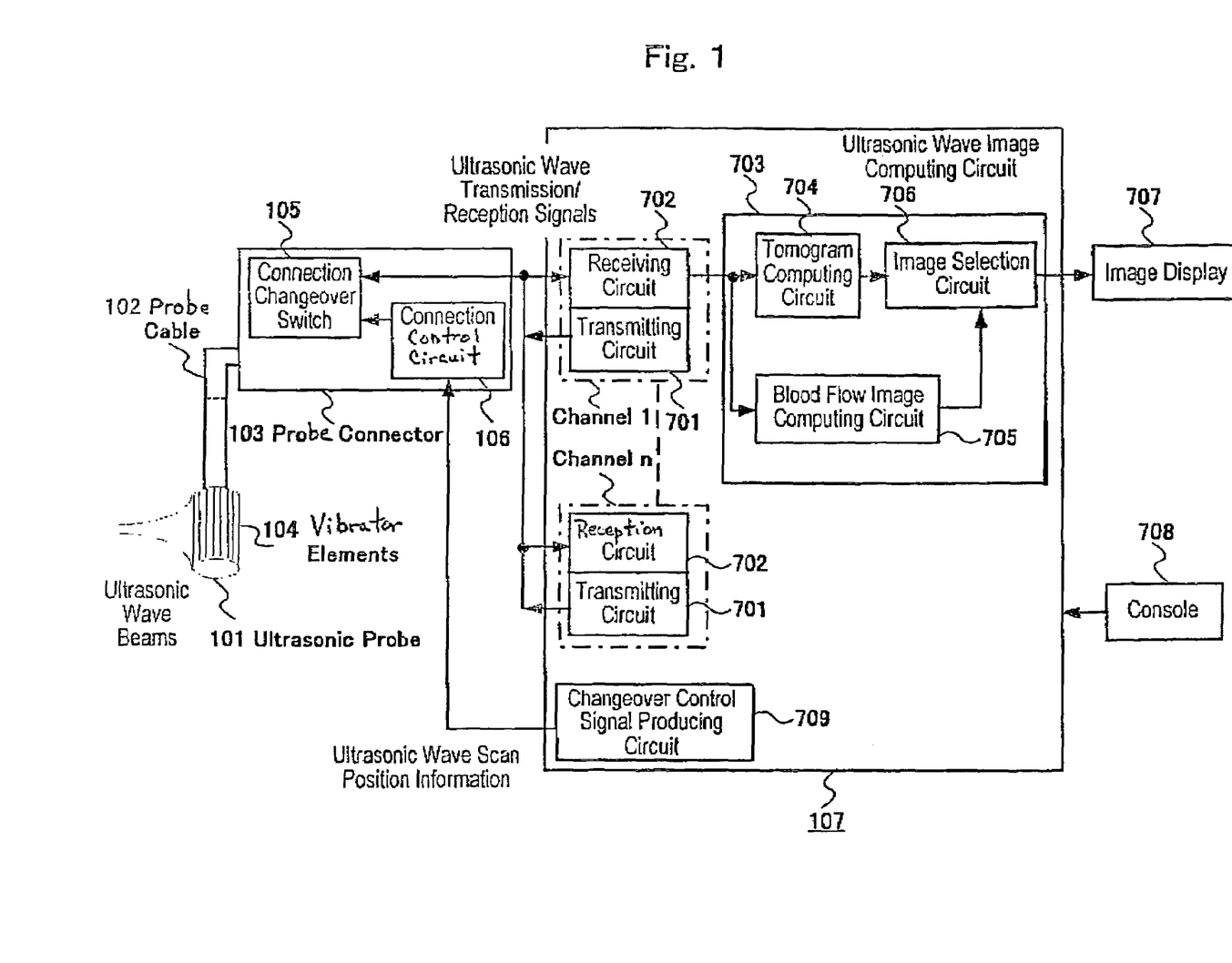
FIG. 1 is a block diagram for explaining a schematic constitution of an ultrasonic diagnostic apparatus representing embodiment 1 of the present invention.

FIG. 1 is a block diagram for explaining a schematic constitution of an ultrasonic probe and an ultrasonic diagnostic apparatus using the same representing embodiment 1 of the present invention, wherein 101 is an ultrasonic probe, 102 probe cables, 103 a probe connector unit, 104 vibrator elements, 105 a change over switch, 106 a connection control circuit and 107 an ultrasonic diagnostic apparatus main body. Although in the present embodiment an example wherein number of ultrasonic wave transmission and reception channels, each is constituted by a signal transmission circuit including a transmission wave phasing circuit and a signal reception circuit including a reception wave phasing circuit, is 32 and the number of the vibrator elements 104 is 256 will be explained, the number of channels of the signal transmission circuit including a transmission wave phasing circuit and the signal reception circuit including a reception wave phasing circuit and the number of vibrator elements are not limited thereto.

As shown in FIG. 1, the ultrasonic diagnostic apparatus according to embodiment 1 is constituted, for example, by the body cavity use ultrasonic probe 101 which is inserted into a subject not shown and is provided with the vibrator elements 104 which transmit ultrasonic waves to the subject as well as receive reflection waves of the transmitted ultrasonic waves and convert the same into electrical signals (herein after will be called as "received wave signals"), and the ultrasonic diagnostic apparatus main body 107 provided with n pieces of ultrasonic wave transmission and reception channels, each consisting by a transmission circuit 701 including a phasing circuit which transmits ultrasonic wave signals after performing focus processing of transmission waves to the vibrator elements 104 based on a measurement condition and a reception circuit 702 including a phasing circuit which performs focus processing of reception waves output from the vibrator elements 104, an ultrasonic wave processing circuit 703 for processing ultrasonic wave images by making use of the received signals output from the respective reception circuits 702, an image display 707, for example, a monitor, which displays such as measurement condition and ultrasonic image information output from the ultrasonic wave processing circuit 703, a well known console 708 which performs such as inputting of the measurement condition and a change over control signal producing circuit 709 which produces a signal (change over control signal) for controlling the connection change over switch 105 in synchronism with the ultrasonic wave transmission and reception. The change over control signal producing circuit 709 produces ultrasonic wave scanning position information (transmission and reception wave direction address) representing information of designating vibrator elements 104 that transmit and receive ultrasonic waves.

The ultrasonic probe 101 according to embodiment 1 is a body cavity use ultrasonic probe comprising a handle portion and an insert portion (herein after will be called an insert section) and is constituted in such a manner that the vibrator elements 104 are disposed around the entire circumference of the tip of the insert section. In particular, as shown in FIG. 1, the ultrasonic probe 101 according to embodiment 1 is constituted in such a manner that a plurality of vibrator elements are arranged in parallel on the outer circumference of the insert section in the direction along the center axis to form a vibrator group and the vibrator group is disposed over the entire 360 degree circumference around the center axis of the insert section, in that with reference to the center axis.

To the respective vibrator elements 104, one of probe cables in total number of 256 is connected which supplies electric power for driving the same as well as functions as a signal line which outputs a received wave signal induced in response to an ultrasonic wave received by the concerned vibrator element 104. The probe cables 102 are constituted to pass inside the insert section and the other ends thereof are connected to the connection change over switch 105 of the probe connector unit 103.

The connection change over switch 105 is constituted so as to be supplied of transmission wave signals from the ultrasonic diagnostic apparatus main body 107. Further, the connection change over switch 105 is input of a change over signal from the connection control circuit 106. Accordingly, during signal transmission, the connection change over switch 105 is constituted to change over vibrator elements 104 to which transmission signals from the ultrasonic wave transmission and reception channels in the ultrasonic diagnostic apparatus main body 107 are supplied based on a change over signal. Likely, during signal reception, the connection change over switch 105 is constituted to change over ultrasonic wave transmission and reception channels to which reception signals from the vibrator elements 104 are supplied based on a change over signal. However, as will be explained later, the connection control circuit 106 changes over the connection change over switch 105 based on ultrasonic wave scanning position information from the ultrasonic diagnostic apparatus main body 107.

Figure 2:
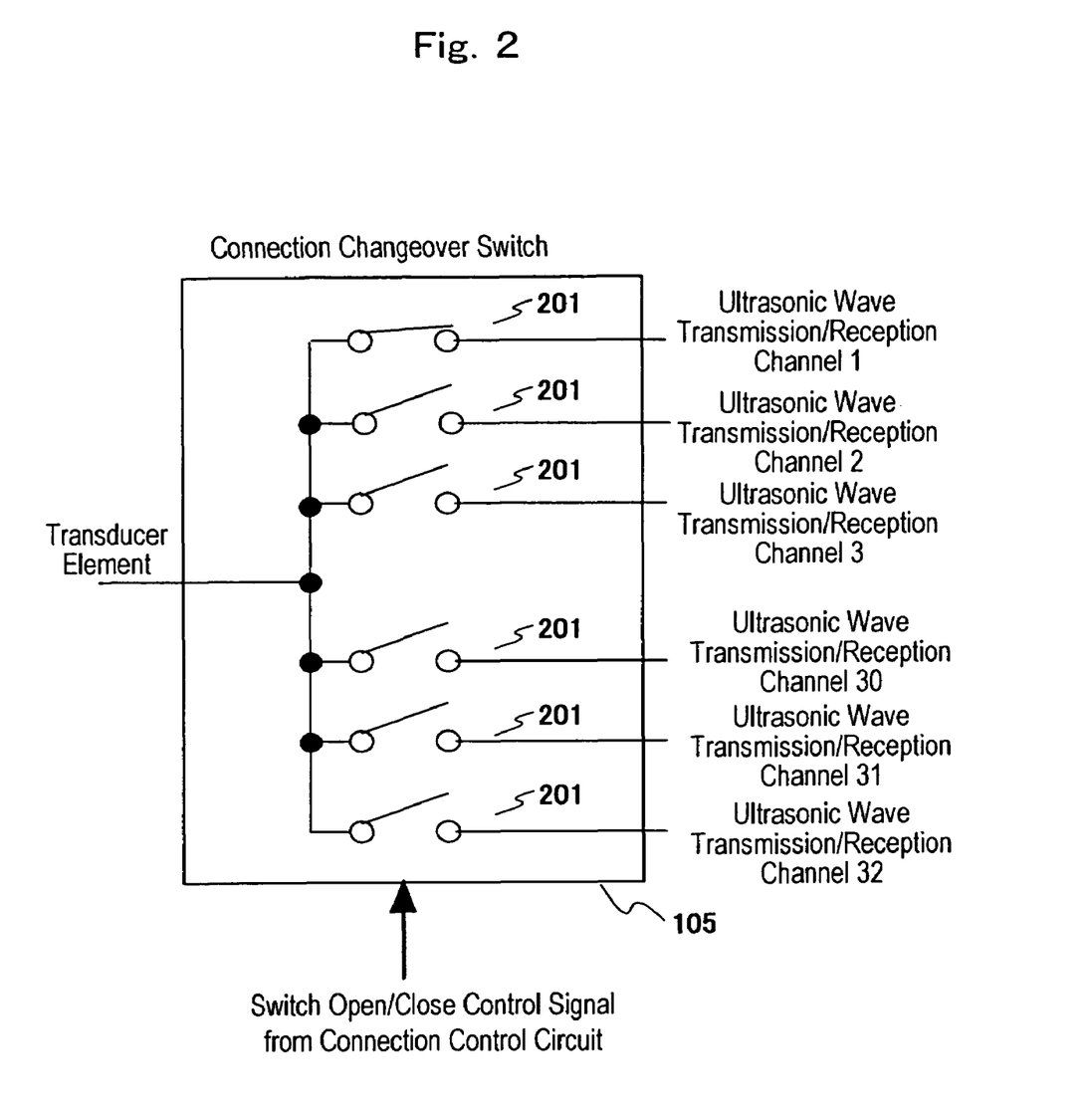
FIG. 2 is a circuit diagram for explaining a schematic constitution of a connection change over switch applied to the ultrasonic diagnostic apparatus according to embodiment 1.

As will be seen from the above, the ultrasonic probe 101 according to embodiment 1 is constituted in a manner that an ultrasonic wave transmission and reception control means including the connection change over switch 105 and the connection control circuit 106 is disposed in the probe connector unit 103 at the handle side of the ultrasonic probe 101. As shown in FIG. 2, the connection change over switch 105 constituting the probe connector unit 103 is constituted by 32 pieces of well known switching elements 201 connected in parallel for changing over ON/OFF for each of the vibrator elements 104. Namely, the connection change over switch 105 according to embodiment 1 is constituted so that the respective vibrator elements 104 are connectable with all of n pieces of ultrasonic wave transmission and reception channels, in that through rendering all of the switching elements 201 in OFF state or only rendering any one of 32 pieces of switching elements 201 in ON state, use and non-use of the concerned vibrator element 104 is changed over.

Further, the connection control circuit 106 constituting the probe connector unit 103 is constituted to include, for example, a well known ROM (Read Only Memory) not shown, and through storing a relationship between ultrasonic wave scanning position information and connection change over switch 105 from the ultrasonic diagnostic apparatus main body 107 in a form of table data, the connection control circuit 106 functions to render only one corresponding switching element 201 in ON state based on the ultrasonic wave scanning position information from the main body and to hold other switching elements 201 in OFF state. Namely, the connection control circuit 106 according to embodiment 1 is constituted to include a retrieving means not shown which retrieves the table data stored in the ROM based on the ultrasonic wave scanning position information output in synchronism with a transmission signal output from the ultrasonic diagnostic apparatus main body 107 and a switching means not shown which ON/OFF controls respective switching elements 201 constituting the connection change over switch 105 based on the date (switch selection information) obtained by the retrieval.

As will be seen from the above, with the ultrasonic diagnostic apparatus according to embodiment 1, without increasing the number of the ultrasonic wave transmission and reception channels each consisting of signal transmission circuit including transmission wave phasing circuit performing ultrasonic wave transmission and a signal receiving circuit including a receiving wave phasing circuit performing wave reception, ultrasonic wave images using 256 pieces of vibrator elements 104 which is more than 32 channels can be collected. Further, through properly connecting the ultrasonic wave transmission and reception channels with the vibrator elements 104 by the connection change over switch 105, the vibrator elements 104 that are to be engaged with the ultrasonic wave transmission and reception are successively changed over. With such constitution, number of the ultrasonic wave transmission and reception channels that was conventionally increased depending on the number of the vibrator elements can be reduced.

Figure 3A:
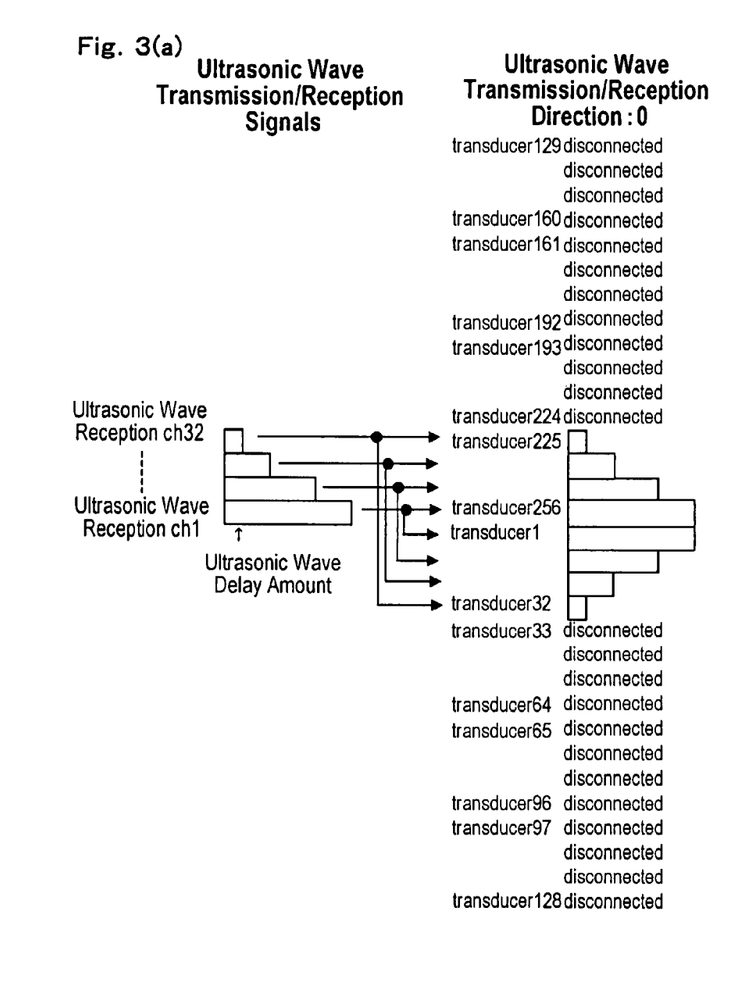
FIG. 3 is a diagram for explaining the change over operation of the connection change over switch in the ultrasonic diagnostic apparatus according to embodiment 1.
Figure 3B:
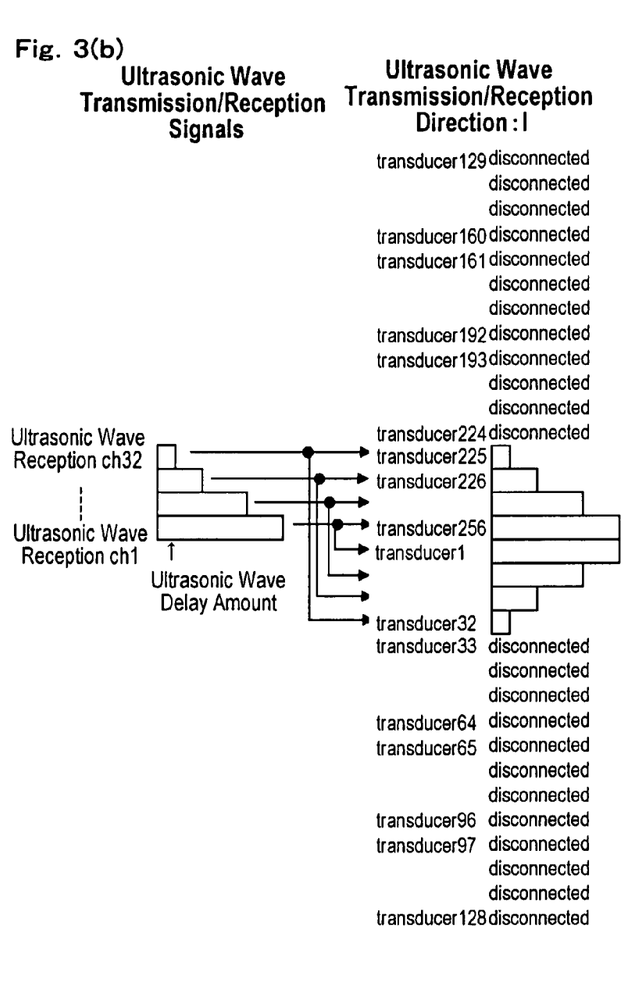

FIG. 3 is a diagram for explaining the change over operation of the connection change over switch 105 in the ultrasonic diagnostic apparatus according to embodiment 1, and, in particular, FIG. 3(*a*) is a diagram for explaining an instance when the address of ultrasonic wave transmission and reception direction is 0 (zero), and FIG. 3(*b*) is a diagram for explaining an instance when the address of ultrasonic wave transmission and reception direction is 1. As shown in FIGS. 3(*a*) and 3(*b*), the vibrator elements are assigned consecutive ID numbers. Although in the arrangement of the vibrator elements as shown in FIGS. 3(*a*) and (*b*), the vibrator elements from the 129th to the 128th are arranged iii one direction, in an actual arrangement, the 128th vibrator is of course arranged adjacent to the 129th vibrator on an circular circumference. Further, in the present embodiment, the upper most address of the transmission and reception direction is 256.

As seen from FIGS. 3(*a*) and (*b*), in the ultrasonic diagnostic apparatus according to embodiment 1, delay times provided for the transmission wave signals and reception wave signals which are necessary for forming ultrasonic wave beams to be transmitted from and received by the ultrasonic wave transmission and reception channels are set only for one side portion of an array of vibrator elements to be driven. In this structure, the connection change over switch is controlled so that the delay time distribution assumes a symmetric form with reference to a vibrator element located at a center of an array of vibrator elements to be driven at respective times.

Namely, in an ultrasonic diagnostic apparatus, relative delay times set for respective vibrator elements during wave transmission and reception are properly adjusted from the past so as to maximize sensitivity at the center of the ultrasonic wave beams (beam center). In particular, through setting the delay time for the vibrator element located at the center among an array of vibrator elements used for the wave transmission and reception the longest and setting delay times for the vibrator elements locating away from the center gradually at shorter times so that artificial distances from the respective vibrator elements to a focus position at the time of wave reception assume the same, an effect is obtained, as if the respective vibrator elements are disposed in a concave shape around the focus position as the center. The bar graphs in FIGS. 3(*a*) and (*b*) show the delay times for the transmission and reception wave signals from the respective channels. Namely, like a conventional manner, using the vibrator element locating at the center as a reference, a same delay time is set for the vibrator elements disposed at the symmetric positions in both sides.

However, as will be apparent from FIGS. 3(*a*) and (*b*), in the ultrasonic diagnostic apparatus according to embodiment 1, each one ultrasonic wave transmission and reception channel is connected to two vibrator elements. Namely, in the ultrasonic diagnostic apparatus according to embodiment 1, as shown in FIG. 3(*a*), the first and 256th vibrator elements are connected to a same ultrasonic wave transmission and reception channel 1. Further, the second and 255th vibrator elements are connected to a same ultrasonic wave transmission and reception channel 2. Likely, until the 32nd and 225th vibrator elements are connected to a same ultrasonic wave transmission and reception channel 32, in total 64 pieces of vibrator elements are connected to any one of 32 pieces of ultrasonic wave transmission and reception channels.

At this instance, in the ultrasonic diagnostic apparatus according to embodiment 1, as will be apparent from the delay times shown by the bar graphs in the drawing, among an array of vibrator elements used for the wave transmission and reception, the delay time of the ultrasonic wave transmission and reception channel 1 which is connected to the first and 256th vibrator elements located at the center is set at the largest value. Thereafter, depending on the distance away from the center, the delay time is gradually shortened and the shortest delay time is set for the ultrasonic wave transmission and reception channel 32 which is connected to the 32nd and 225th vibrator elements to be disposed at the most outsides. Further, in the ultrasonic diagnostic apparatus according to embodiment 1, since the vibrator elements are disposed around the outer circumference at the tip portion of the insert section of the probe, the vibrator elements are geometrically arranged in a convex shape at the side of transmission and reception wave face.

On the other hand, in the ultrasonic diagnostic apparatus according to embodiment 1, since the ultrasonic wave transmission and reception is performed by making use of vibrator elements in maximum of 64 pieces for one time scanning by the ultrasonic wave beams among 256 pieces of vibrator elements, the interval between the 32nd and 225th vibrator elements which are disposed at the outer most side among the vibrator elements used for the transmission and reception is 90 degree with reference to the central axis of the insert section. As will be seen from the above, in the ultrasonic diagnostic apparatus according to embodiment 1, since the vibrator elements are arranged in a convex shape, by determining the number of the vibrator elements used for the ultrasonic wave transmission and reception in one time as 64 pieces, namely, by determining the interval between the outer most vibrator elements as 90 degree, a reduction in efficiency of the ultrasonic wave transmitted and received by the respective outer most vibrator elements is suppressed.

Further, the scanning by ultrasonic wave beams in the ultrasonic diagnostic apparatus according to embodiment 1 is designed, as shown in FIG. 3(b), to collect ultrasonic wave images of entire circumference of the insert section by shifting one by one successively the vibrator elements transmitting and receiving ultrasonic waves. Namely, without changing the setting of the delay times of the ultrasonic wave transmission and reception channels and through controlling the connection change over switch 105, the vibrator elements to be used for the ultrasonic wave transmission and reception are shifted toward the 33rd vibrator elements. Through this shifting, the first and second vibrator elements are connected to a same ultrasonic wave transmission and reception channel 1. Further, the third and 256th vibrator elements are connected to a same ultrasonic wave transmission and reception channel 2. Likely, the connections between the respective ultrasonic wave transmission and reception channels and the vibrator elements are shifted and the 33rd and 226th vibrator elements are connected to a same ultrasonic wave transmission and reception channel 32, in total 64 pieces of vibrator elements are connected to any one of 32 pieces of ultrasonic wave transmission and reception channels.

As has been explained above, since the ultrasonic diagnostic apparatus according to embodiment 1 is constituted to shift the scanning direction without changing the delay times set for the respective transmission and reception channels, the delay time of the transmission and reception wave signal from the ultrasonic wave transmission and reception channel connected to the vibrator element located at the center of the array of vibrator elements used for the ultrasonic wave transmission and reception among the vibrator elements arranged around the outer circumference of the insert section shows the maximum value. Thereafter, depending on the distance away from the center, the delay time is gradually shortened and the shortest delay time is set for the transmission and reception signal from the ultrasonic wave transmission and reception channel which is connected to the 33rd and 226th vibrator elements to be disposed at the most outsides.

Through performing the shifting operation successively in the scanning direction as has been explained above, the ultrasonic diagnostic apparatus according to embodiment 1 can collect ultrasonic wave images over the entire 360 degree outer circumference of the insert section of the ultrasonic probe 101 on which the vibrator elements are arranged.

When inserting the ultrasonic probe according to embodiment 1 into a body cavity such as a rectum or into a stomach via an esophagus, ultrasonic images of entire 360 degree circumference can be obtained in real time, the examiner can easily grasp the situation of disease, the time required for diagnosis can be reduced and the diagnostic efficiency can be enhanced as well as the load to a subject can be reduced.

Now, computation and display of ultrasonic blood flow images at any 360 degree positions in vivo with the ultrasonic diagnostic apparatus according to embodiment 1 will be explained.

Received signals phasing processed by the respective receiving circuits 702 are input into the ultrasonic wave image computing circuit 703. The ultrasonic wave image computing circuit 703 includes inside thereof a tomogram computing circuit 704 for reconstructing tomograms and a blood flow image computing circuit 705 for computing and reconstructing blood flow images and the outputs of the respective receiving circuits 702 are transferred to the tomogram computing circuit 704 and the blood flow image computing circuit 705. The structure and the processing contents of the blood flow image computing circuit 705 are explained in detail in JP-A-61-135639 as referred to above. Further, an image selection circuit 706 is for selecting outputs from the tomogram computing circuit 704 and the blood flow image computing circuit 705 to display either tomograms or blood flow images in a manner to display either tomograms or blood flow images or superposed images of both. The outputs of the image selection circuit 706 are displayed on an image display unit 707 such as a monitor.

Figure 6:
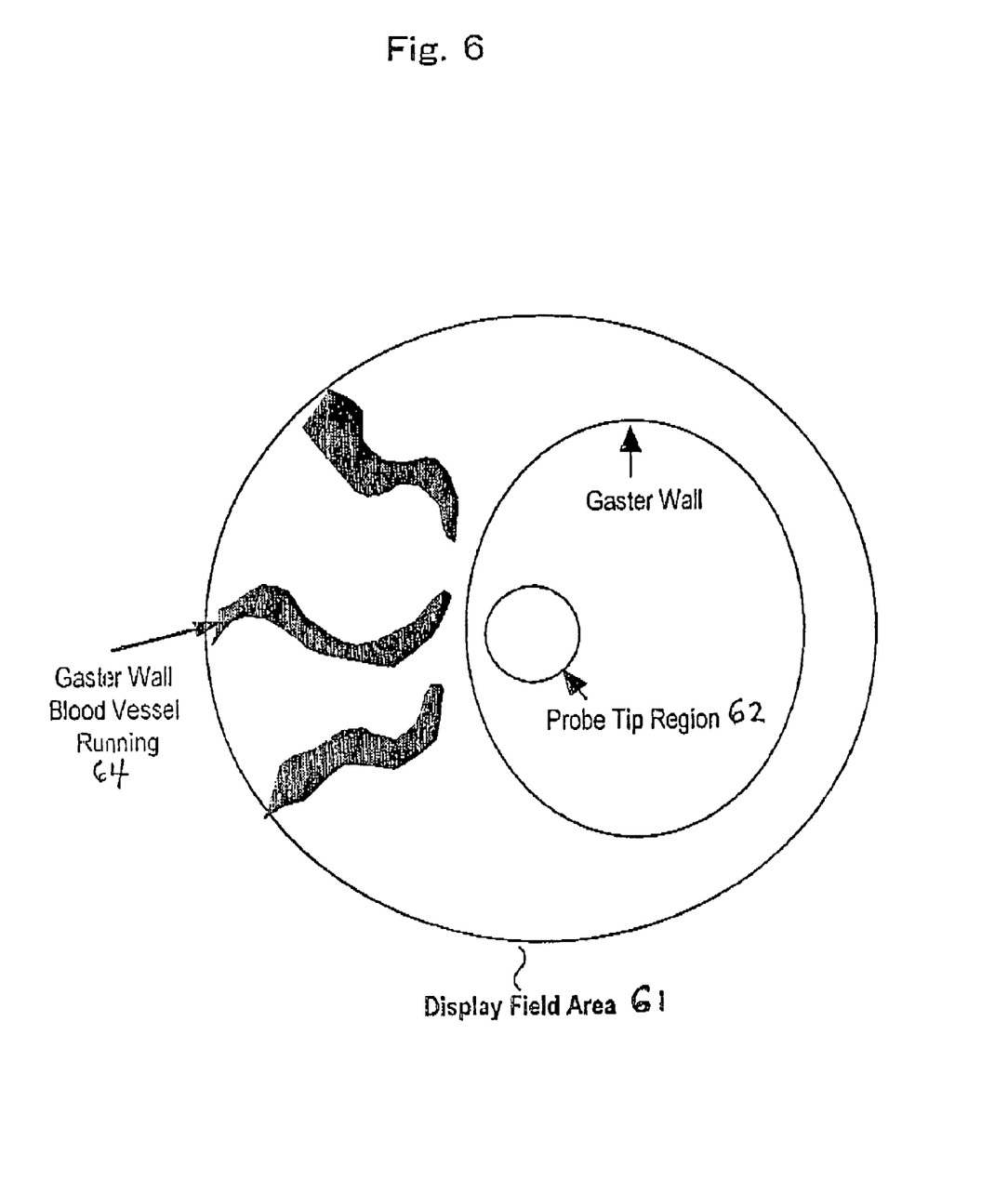
FIG. 6 is a view for explaining a tomographic image including blood steam images obtained by the ultrasonic diagnostic apparatus according to embodiment 1.

FIG. 6 is a view for explaining ultrasonic wave images obtained by the ultrasonic diagnostic apparatus according to embodiment 1, and, in particular, a schematic view of an image (display field area 61) obtained when inserting the Ultrasonic probe according to embodiment 1 into a stomach via an esophagus and measured an ultrasonic tomogram and a two dimensional blood flow image.

In this instant measurement, after introducing the rip portion or the insert section of the ultrasonic probe (shown in FIG. 6 at probe tip region 62) into the stomach, the stomach wall 63 of plural layer structure was observed as well as blood flow kinetics (64) flowing through blood vessels in the stomach wall was observed.

As will be apparent from the measurement result as shown in FIG. 6, by means of the ultrasonic diagnostic apparatus with the ultrasonic probe according to embodiment 1 through inserting the insert section into the body cavity, not only the tomograms over the entire 360 degree circumference but also blood flow information over two dimensions within an in vivo organ can be obtained, therefore, as referred to above, the examiner can easily grasp the situation of disease, the time required for diagnosis can be reduced and the diagnostic efficiency can be enhanced as well as the load to a subject can be reduced.

Embodiment 2

Figure 4:
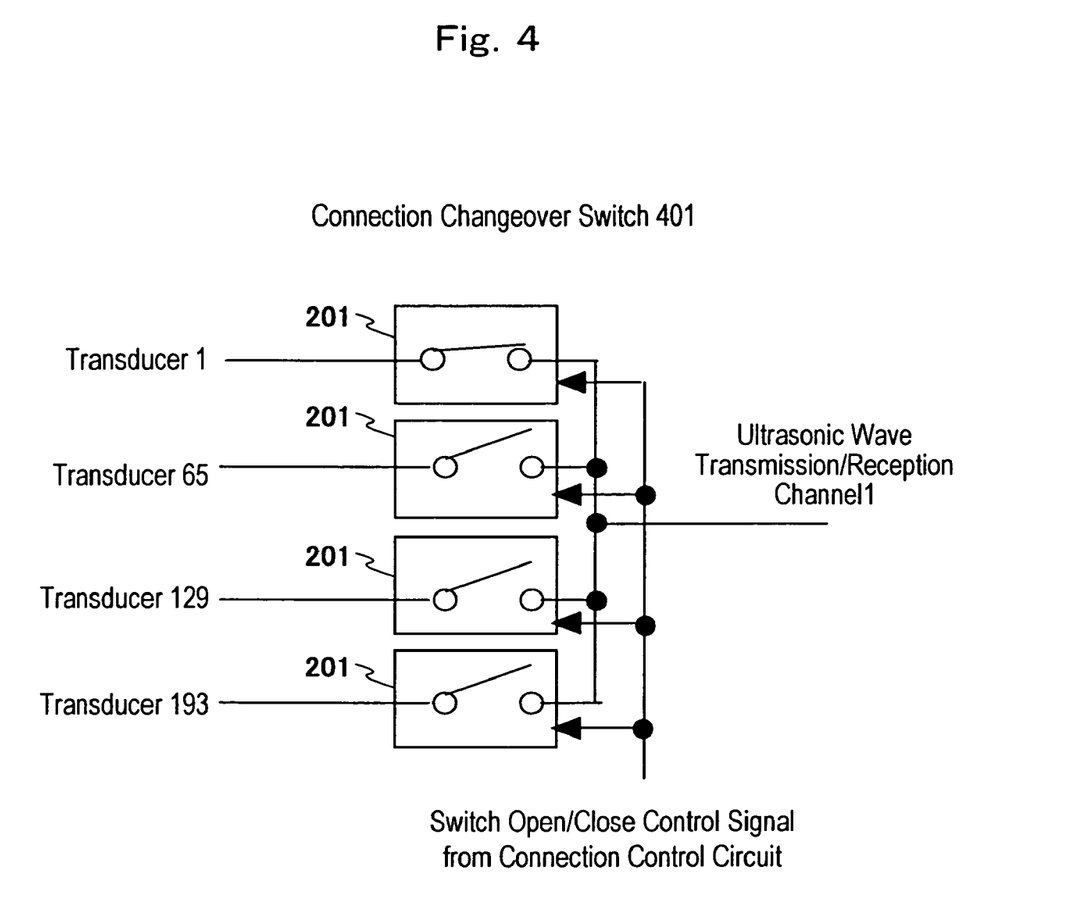
FIG. 4 is a circuit diagram for explaining a schematic constitution of a connection change over switch applied to an ultrasonic diagnostic apparatus according to embodiment 2.

FIG. 4 is a view for explaining a schematic constitution, in particular, of a connection change over switch constituting a probe connector portion in the ultrasonic diagnostic apparatus according to embodiment 2. In the ultrasonic diagnostic apparatus according to embodiment 2, constitutions other than the connection change over switch, the connection control circuit and the ultrasonic wave transmission and reception channels for producing transmission signals and for performing the focus processing of received signals are the same as those in the ultrasonic diagnostic apparatus according to embodiment 1. Accordingly, in the following explanation, only the connection change over switch, the connection control circuit and the ultrasonic wave transmission and reception channels of which constitutions are different from those in the ultrasonic diagnostic apparatus according to embodiment 1 will be explained in detail.

As shown in FIG. 4, a connection change over switch 401 according to embodiment 2 is constituted by a plurality of switching elements 201 connected in parallel so as to be connectable to one ultrasonic wave transmission and reception channel, and to each of the switching elements 201 a predetermined one vibrator element is connected. In particular, in the ultrasonic diagnostic apparatus according to embodiment 2, four switching elements 201 are arranged for one specific ultrasonic transmission and reception channel, for example, the four switching elements 201 of the first, 56th, 129th and 193rd vibrator elements are arranged to be connectable to the first ultrasonic wave transmission and reception channel.

Namely, in embodiment 1, 32 pieces of switching elements 201 are connected to one vibrator element 104, therefore, 256 vibrator elements×32 pieces=8192 pieces of switching elements are required. On the other hand, in embodiment 2, to one ultrasonic wave transmission and reception channel four pieces of switching elements 201 are arranged to be connectable thereto, therefore, only 256 pieces of switching elements are required.

Further, even in the connection change over switch 401 in embodiment 2, ON/OFF of the respective switching elements 201 is controlled based on control signals from a connection control circuit not shown.

Figure 5A:
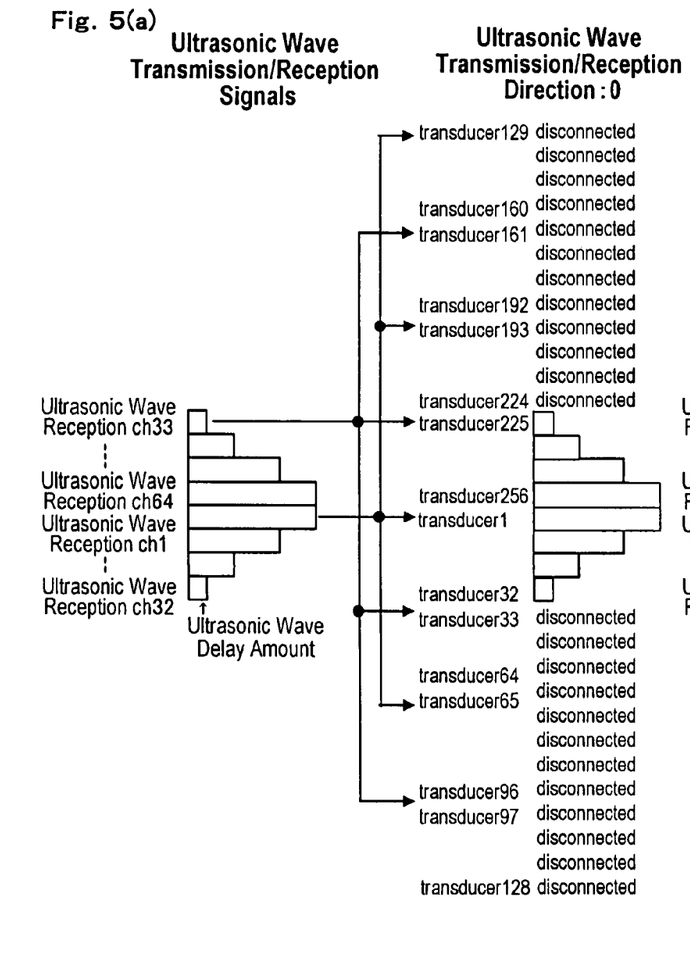
FIG. 5 is a diagram for explaining the change over operation of the connection change over switch in the ultrasonic diagnostic apparatus according to embodiment 2.
Figure 5B:
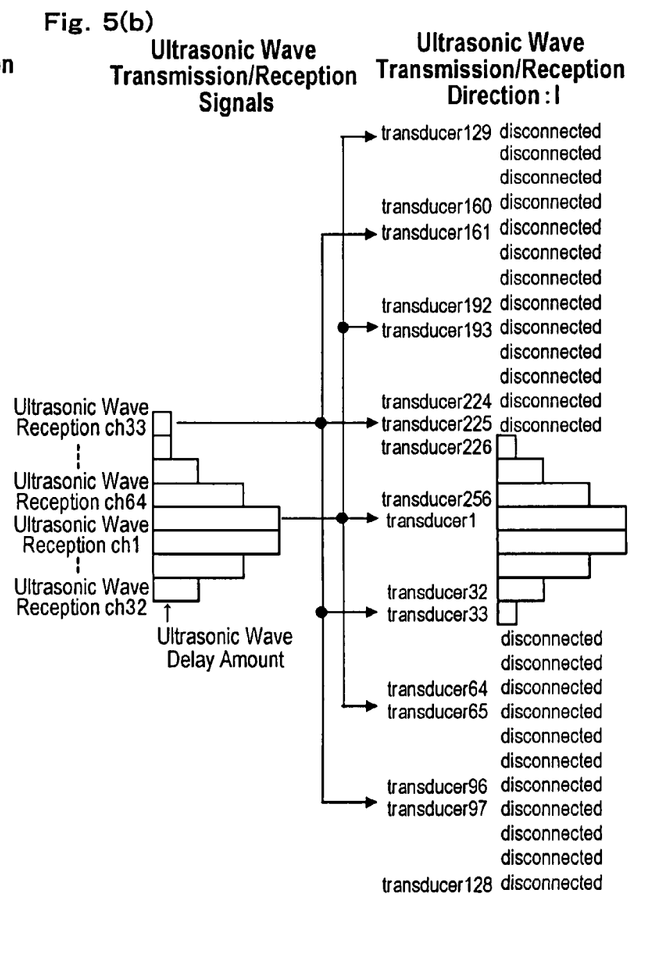

FIG. 5 is a diagram for explaining the change over operation of the change over switch in the ultrasonic diagnostic apparatus according to embodiment 2 and, in particular, FIG. 5(a) is a diagram for explaining the operation when the address of ultrasonic wave transmission and reception direction is 0 (zero) and FIG. 5(b) is a diagram for explaining the operation when the address of ultrasonic wave transmission and reception direction is 1. Although in the arrangement of the vibrator elements as shown in FIGS. 5(a) and (b), the vibrator elements from the 129th to the 128th are arranged in one direction, in an actual arrangement, the 128th vibrator is of course arranged adjacent to the 129th vibrator on an circular circumference as in the ultrasonic diagnosis device according to embodiment 1.

As shown in FIGS. 5(a) and (b), in the ultrasonic diagnostic apparatus according to embodiment 2, number of 64 ultrasonic wave transmission and reception channels is required so that the delay times provided for transmission and reception signals necessary for the ultrasonic wave beam formation cover both side portions instead of the one side portion.

In the ultrasonic diagnostic apparatus according to embodiment 2, as shown in FIG. 5(a), the first, 65th, 129th and 193rd vibrator elements are arranged to be connectable to the first ultrasonic transmission and reception channel via the switching elements 201 as shown in FIG. 4. In this instance, when the address of the ultrasonic wave transmission and reception direction is 0 (zero), among the switching elements which are connectable to the first ultrasonic wave transmission channel, only the switching element connected to the first vibrator element is rendered to ON state (conductive state), and the first ultrasonic wave transmission and reception channel and the first vibrator element are electrically connected. Further, the second, 66th, 130th and 194th vibrator elements not shown are respectively arranged to be connectable to the second ultrasonic transmission and reception channel via the switching elements 201 not shown. Likely, the 33rd, 97th, 161st and 225th vibrator elements are arranged to be connectable to the 33rd ultrasonic transmission and reception channel via the switching elements not shown and the 64th, 128th, 192nd and 256th vibrator elements are arranged to be connectable to the 64th ultrasonic transmission and reception channel via the switching elements not shown.

In this instance, in the ultrasonic diagnostic apparatus according to embodiment 2, the delay times set for the respective ultrasonic wave transmission and reception channels vary as shown by the bar graphs in the drawing. In FIG. 5(a), as will be apparent from the bar graphs, among the array of vibrator elements used for the wave transmission and reception (first~32nd and 225th~256th vibrator elements), the delay time of the transmission and reception wave signal from the ultrasonic wave transmission and reception channel connected to the first and 256th vibrator elements located at the center is set at the maximum value. Thereafter, depending on the distance away from the center, the delay time is gradually shortened and the shortest delay time is set for the transmission and reception signal from the ultrasonic wave transmission and reception channel which is to be connected to the 32nd and 225th vibrator elements to be disposed at the most outsides. Further, also in the ultrasonic diagnostic apparatus according to embodiment 2, since the vibrator elements are disposed around the cylindrical outer circumference at the tip portion of the insert section of the probe, the vibrator elements are geometrically arranged in a convex shape at the side of transmission and reception wave face, however, since the delay times are set for the respective vibrator elements as shown in the bar graph, the effect as if the vibrator elements are arranged on a concave face with reference to the focus position as the center like in the ultrasonic diagnostic apparatus according to embodiment 1.

Further, the scanning with the insert section in an organ in vivo by ultrasonic wave beams in the ultrasonic diagnostic apparatus according to embodiment 2 is designed, as shown in FIG. 5(b), to collect ultrasonic wave images of entire circumference of the insert section by shifting one by one successively the vibrator elements transmitting and receiving ultrasonic waves.

Namely, while setting for the first ultrasonic wave transmission and reception channel the same ultrasonic wave delay amount as that of immediately before for the 64th ultrasonic wave transmission and reception channel, the connection control circuit 106 controls the connection change over switch 401 so as to hold the connection to the first vibrator element and effects the ultrasonic wave transmission and reception for the first vibrator element.

Likely, while setting for the second ultrasonic wave transmission and reception channel the same ultrasonic wave delay amount as that of immediately before for the first ultrasonic wave transmission and reception channel, the connection control circuit 106 controls the connection change over switch 401 so as to hold the connection to the second vibrator element and effects the ultrasonic wave transmission and reception for the second vibrator element. Further, the like operation is performed up to the 32nd ultrasonic wave transmission and reception channel.

At the moment when the immediately before address was zero, the connection control circuit 106 performed a control so that the 33rd ultrasonic wave transmission and reception channel performed signal transmission and reception for the 225th vibrator element by turning ON a switch element 201 constituting the connection change over switch 401 and did not perform ultrasonic wave signal transmission and reception for the 161st, 33rd, and 97th vibrator elements by turning OFF switches 201 constituting the connection change over switch 401.

Due to the shifting of the ultrasonic wave transmission and reception position by one, while setting for the 33rd ultrasonic wave transmission and reception channel the same ultrasonic wave delay amount as that of immediately before for the 32nd ultrasonic wave transmission and reception channel, the connection control circuit 106 controls the connection change over switch 401 to effect the ultrasonic wave transmission and reception for the 33rd vibrator element as well as not to effect the ultrasonic wave transmission and reception for the 161st, 225 and 97th vibrator elements.

Further, for the 34th~64th ultrasonic wave transmission and reception channels, while setting the ultrasonic wave delay times being shifted by one of those of immediately before, the connection control circuit 106 controls the connection change over switch 401 to effect ultrasonic wave signal transmission and reception for the same vibrator elements as those of immediately before.

Summing up the above, while setting the ultrasonic wave delay times for the ultrasonic wave transmission and reception channels by shifting from those of the immediately before by one, the connection control circuit 106 controls the connection change over switch 401 so that a newly connected vibrator element is shifted by one in the scanning direction and the most rear end vibrator element is disconnected.

Through performing the above explained operation successively, ultrasonic diagnostic apparatus according to embodiment 2 can likely collect ultrasonic wave images over the entire 360 degree outer circumference of the insert section of the ultrasonic probe on which the vibrator elements are arranged.

Although in embodiments 1 and 2, an example wherein a number of vibrator elements in an array of the ultrasonic wave vibrator elements driven at a time is 64 has been explained, the arrangement of the ultrasonic wave transmission and reception channels and the connection change over switch can be modified depending on the depth of the portion of a body cavity organ desired for imaging, for example, when focusing the ultrasonic wave beams to a deep portion remote from the ultrasonic probe, an array of 96 pieces of vibrator elements are selected which are driven at one time, and on the contrary when focusing the ultrasonic wave beams to a shallow portion near from the ultrasonic probe, an array of 32 pieces of vibrator elements are selected which are driven at one time.

The invention claimed is:

1. An ultrasonic probe comprising an insert section which is to be inserted into a body cavity organ of a subject and a handle section which couples with the insert section, wherein a first predetermined number of vibrator elements are disposed in an array at the tip of the insert section around entire 360 degree outer circumference thereof and a connection change over switch is disposed, and the connection change over switch successively changes over electrical connection of a second predetermined number of vibrator elements among the first predetermined number of vibrator elements to be connected with a third predetermined number of ultrasonic wave transmission and reception channels, in which each of the second predetermined number and the third predetermined number is smaller than the first predetermined number, and each of the plurality of vibrator elements in the array is assigned a consecutive ID number, and the connection change over switch connects a first vibrator element having a lowest ID number and a second vibrator element having a highest ID number to respective corresponding ultrasonic wave transmission and reception channels each having a predetermined delay time so as to permit successive scanning of the plurality of vibrator elements, from the first vibrator element having the lowest ID number in an order of increasing ID number through remaining vibrator elements in the array to the second vibrator element having the highest ID number, and then from the second vibrator element having the highest ID number to the first vibrator element having the lowest ID number, wherein the connection change over switch is constituted in such a manner that each of the third predetermined number of the ultrasonic wave transmission and reception channels is connectable with the first predetermined number of the vibrator elements at the second predetermined number of channel intervals, the delay times of the ultrasonic wave signals transmitted and received from the third predetermined number of ultrasonic wave transmission and reception channels are set changeable at respective times, and each of the second predetermined number and the third predetermined number is greater than one, and wherein the connection change over switch is configured for each of the third predetermined number of ultrasonic wave transmission and reception channels to be connectable to a corresponding subset of plural ones of the vibrator elements, and a number, equal to the second or third predetermined number, of vibrator elements are used to focus ultrasonic wave beams at a time.

2. An ultrasonic diagnostic apparatus comprising an ultrasonic probe having an insert section which is to be inserted into a body cavity organ of a subject and a handle section which couples with the insert section, wherein a first predetermined number of vibrator elements are disposed in an first array at the tip of the insert section around entire 360 degree outer circumference of the ultrasonic probe, and an ultrasonic diagnostic apparatus main body having a third predetermined number of ultrasonic wave transmission and reception channels for transmitting and receiving ultrasonic wave signals to the ultrasonic probe and an ultrasonic wave image computing circuit for computing ultrasonic images based on the ultrasonic wave transmission and reception signals from the third predetermined number of ultrasonic wave transmission and reception channels, a connection change over switch is disposed, and the ultrasonic wave image computing circuit in the ultrasonic diagnostic apparatus main body includes an ultrasonic tomogram computing circuit and an ultrasonic blood flow image computing circuit, and the connection change over switch successively changes over electrical connection of a second predetermined number of vibrator elements among the first predetermined number of vibrator elements to be connected with the third predetermined number of ultrasonic wave transmission and reception channels and is ON and OFF controlled so that the delay time of ultrasonic wave signal transmitted and received by a vibrator element located at the center of a second array of the second predetermined number of the vibrator elements being connected at respective times assumes the maximum and the delay times of ultrasonic wave signals transmitted and received are distributed in a symmetric manner with reference to the center, in which each of the second predetermined number and the third predetermined number is smaller than the first predetermined number, each of the plurality of vibrator elements in the first array is assigned a consecutive ID number, and the connection change over switch connects a first vibrator element having a lowest ID number and a second vibrator element having a highest ID number to respective corresponding ultrasonic wave transmission and reception channels each having a predetermined delay time so as to permit successive scanning of the plurality of vibrator elements, from the first vibrator element having the lowest ID number in an order of increasing ID number through remaining vibrator elements in the first array to the second vibrator element having the highest ID number, and then from the second vibrator element having the highest ID number to the first vibrator element having the lowest ID number,
wherein the connection change over switch is constituted in such a manner that each of the third predetermined number of the ultrasonic wave transmission and reception channels is connectable with the first predetermined number of the vibrator elements at the second predetermined number of channel intervals,
the delay times of the ultrasonic wave signals transmitted and received from the third predetermined number of ultrasonic wave transmission and reception channels are set changeable at respective times,
each of the second predetermined number and the third predetermined number is greater than one, and
wherein the connection change over switch is configured for each of the third predetermined number of ultrasonic wave transmission and reception channels to be connectable to a corresponding subset of plural ones of the vibrator elements, and a number, equal to the second or third predetermined number, of vibrator elements are used to focus ultrasonic wave beams at a time.

3. An ultrasonic diagnostic apparatus according to claim 2, wherein the predetermined number of the vibrator elements connected to the predetermined number of the ultrasonic wave transmission and reception channels at respective times by the connection change over switch is that which covers about 90 degrees over the outer circumferential face at the tip of the insert section.

4. An ultrasonic diagnostic apparatus according to claim 2, wherein the ultrasonic wave image computing circuit further includes an image selection circuit.

5. An ultrasonic diagnostic apparatus according to claim 2, wherein the predetermined number of the vibrator elements connected to the predetermined number of the ultrasonic wave transmission and reception channels at respective times by the connection change over switch is variable depending on the depth of a portion of a body cavity organ for image taking.

6. An ultrasonic diagnostic apparatus according to claim 2, wherein the ultrasonic diagnostic apparatus main body further includes an image display unit which displays an ultrasonic tomogram and an ultrasonic blood flow image based on outputs from the ultrasonic tomogram computing circuit and the ultrasonic blood flow image computing circuit.

7. An ultrasonic diagnostic apparatus according to claim 2, wherein the successive change over of the electrical connection by the connection change over switch of the predetermined number of the ultrasonic wave transmission and reception channels with the array of the predetermined number of vibrator elements is performed by repeating an operation of disconnecting the rear most vibrator element among the array of the predetermined number of the vibrator elements in the scanning direction by the ultrasonic wave signals with an ultrasonic wave transmission and reception channel and of newly connecting a vibrator element adjacent to the top vibrator element among the array of the predetermined number of the vibrator elements in the scanning direction by the ultrasonic wave signals with the ultrasonic wave transmission and reception channel of which connection with the rear most vibrator element was disconnected immediately before.

8. An ultrasonic diagnostic apparatus according to claim 7, wherein the successive change over of the electrical connection by the connection change over switch of the predetermined number of the ultrasonic wave transmission and reception channels with the array of the predetermined number of vibrator elements is performed by shifting the scanning direction by the ultrasonic wave signals over the entire 360 degree circumference.

9. An ultrasonic diagnostic apparatus according to claim 2, wherein the delay times of the ultrasonic wave signals transmitted and received from the first predetermined number of ultrasonic wave transmission and reception channels are shifted from those immediately before by one in accordance with the time changes.

* * * * *

UNITED STATES PATENT AND TRADEMARK OFFICE
CERTIFICATE OF CORRECTION

PATENT NO. : 7,691,065 B2  
APPLICATION NO. : 10/563086  
DATED : April 6, 2010  
INVENTOR(S) : Satoshi Tamano et al.

It is certified that error appears in the above-identified patent and that said Letters Patent is hereby corrected as shown below:

Title Page, Item (75)  
Replace the Inventors section on the cover page of the patent, with the following:

-- (75) Inventors: Satoshi Tamano, Chiba (JP); Akihiko Hanaoka, Ibaraki (JP); Hideki Okazaki, Chiba (JP); Takashi Kobayashi, Chiba (JP); Sachie Yoshida, Chiba (JP) --

Signed and Sealed this  
Fifteenth Day of November, 2011

David J. Kappos  
*Director of the United States Patent and Trademark Office*